(12) United States Patent
Aida et al.

(10) Patent No.: US 6,949,620 B2
(45) Date of Patent: Sep. 27, 2005

(54) POLYMERIC MICELLAR STRUCTURE

(75) Inventors: Takuzo Aida, Kashiwa (JP); Dong-Lin Jiang, Matsudo (JP); Daisuke Ohno, Tokyo (JP); Hendrick Stapert, Eindhoven (JP); Nobuhiro Nishiyama, Tokyo (JP); Kazunori Kataoka, Kashiwa (JP)

(73) Assignee: Japan Science and Technology Corporation, Saitama (JP)

( * ) Notice: Subject to any disclaimer, the term of this patent is extended or adjusted under 35 U.S.C. 154(b) by 260 days.

(21) Appl. No.: 10/182,191
(22) PCT Filed: Jan. 26, 2001
(86) PCT No.: PCT/JP01/00546
§ 371 (c)(1),
(2), (4) Date: Oct. 18, 2002
(87) PCT Pub. No.: WO01/55151
PCT Pub. Date: Aug. 2, 2001

(65) Prior Publication Data
US 2003/0153547 A1 Aug. 14, 2003

(30) Foreign Application Priority Data
Jan. 26, 2000 (JP) ........................... 2000-017662
Jan. 26, 2000 (JP) ........................... 2000-017663

(51) Int. Cl.[7] ................ C08G 79/00; C08G 69/10
(52) U.S. Cl. ............. 528/395; 528/328; 528/310; 528/424; 528/425; 525/419; 525/420
(58) Field of Search ................ 528/395, 328, 528/300, 424, 425; 525/419, 420

(56) References Cited
FOREIGN PATENT DOCUMENTS
JP 4-505612 10/1992

OTHER PUBLICATIONS

Sadamoto et al; Photoinduced electron transfer reactions through dendrimer architectures; 1996; Chem Abstract 124: 302161.*
Stapert et al., Langmuir, vol. 16, pp. 8182–8188 (2000).
Jiang et al., Kobunshi Ronbunshu, vol. 54 (10), pp. 674–683 (1997).

* cited by examiner

Primary Examiner—Duc Truong
(74) Attorney, Agent, or Firm—Wenderoth, Lind & Ponack, L.L.P.

(57) ABSTRACT

The invention relates to a polymeric micellar structure which comprising an ionic porphyrin dendrimer represented by general formula (1): q(c)PM (where q represents the number of charged atoms on the periphery of the dendrimer; c represents a negative (−) or positive (+) charge; and PM is represented by the following general formula (2):

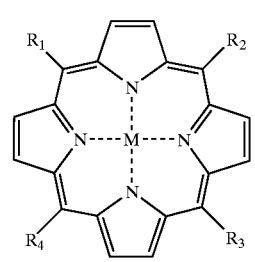

wherein M represents two hydrogen atoms or a metal atom, $R_1$, $R_2$, $R_3$ and $R_4$ are the same or different and represents hydrogen or identical or different aryl ether dendrosubunits, provided that at least one of $R_1$, $R_2$, $R_3$ and $R_4$ represent an aryl ether dendrosubunits and that each aryl ether dendrosubunit has an anionic or cationic group at the end optionally though a spacer molecule chain.

12 Claims, 2 Drawing Sheets

POLYMERIC MICELLAR STRUCTURE

TECHNICAL FIELD

The invention of this application relates to a polymeric micellar structure. More specifically, the invention of this application relates to a polymeric micellar structure comprising an ionic porphyrin dendrimer, which may be used in photodynamic treatment.

BACKGROUND ART

At present, most treatments that use chemical drugs or radiation for cancers or tumors affect tissue cells other than the target sites, and cause side effects such as aches, pyrexia and vomiting, and have therefore caused much suffering for patients. Further, secondary tumors resulting from the destruction of surrounding cells by drugs and radiation used in such treatments are becoming serious problems.

Accordingly, in recent years, increasing studies are being made on drugs for treatment of cancer and tumors with less side effects and on drug delivery systems, which allow drugs to be delivered directly to the target cancerous cells.

Among such recent findings, photodynamic treatment is a method wherein a target site is treated by incorporating into the body a compound that reacts with light such as ultraviolet light, visible light and infrared and irradiating the target site. Because the compound does not react without the irradiation of light, or at areas that are not irradiated, and only the cancerous cells at the target site are selectively destructed, the method has attracted much interest.

In such photodynamic treatment, photoreactive compounds that show high affinity to tumors and undergo photoexcitation in high yield are desired. Porphyrin compounds comprising a porphyrin ring are one type of photoreactive compounds known for photodynamic treatment. That is, porphyrin compounds react with ambient oxygen molecules by the irradiation of light, and through photoexcitation, convert them to singlet oxygen with high oxidative strength, which then oxidizes and destroys the surrounding cells.

Accordingly, oligomeric compounds having a porphyrin ring bound thereto and compounds comprising sugar chains, DNA, proteins or the like bonded to porphyrin have been proposed, and studies to accomplish higher cell recognition ability and tumor affinity are underway. However, many porphyrin compounds have been problematic in that they show high toxicity even without irradiation and often destroy cells other than those at the target site. Further, since the efficiency of the photoreaction and the affinity to tumor is low, it was necessary to inject high doses of the compound to the body, making the compounds far from desirable.

With respect to the foregoing problems, the present inventors have proposed, as compounds for photodynamic treatment, ionic porphyrin compounds which show low toxicity in vivo and destroy cancerous cells at the target site without attacking the surrounding cello (Japanese Patent Application 2000-17663). In practice, however, these compounds as dendrimers showed insufficient solubility in blood; in order to use the ionic porphyrin compounds as anticancer drugs in photodynamic treatment, it is required that these compounds show stability and efficiency in blood and are reliably delivered to the target site.

The invention of this application has been made under the foregoing circumstances, and upon solving the problems of the ordinary art, its object is to provide a polymeric micellar structure, which is capable of efficiently delivering the porphyrin compound for photodynamic treatment to the target cells, easy to use as a drug, and stable in water.

DISCLOSURE OF THE INVENTION

In order to solve the problems of the prior art, the invention of the present application provides the following inventions.

That is, the present invention firstly provides a polymeric micellar structure comprising an ionic porphyrin dendrimer represented by general formula [1]

$$q(c)PM \quad [1]$$

(wherein q represents the number of charged atoms on the periphery of the dendrimer, c represents a negative (−) or positive (+) charge; and PM is represented by the following general formula [2];

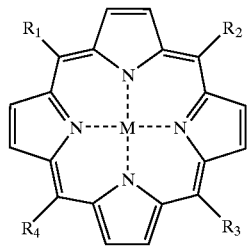

[2]

wherein M represents two hydrogen atoms or a metal atom, $R_1$, $R_2$, $R_3$ and $R_4$ represent a hydrogen atom or aryl ether dendro-subunits that may be identical or different, at least one of $R_1$, $R_2$, $R_3$ and $R_4$ is an aryl ether dendro-subunit, which is represented by the following general formula [3];

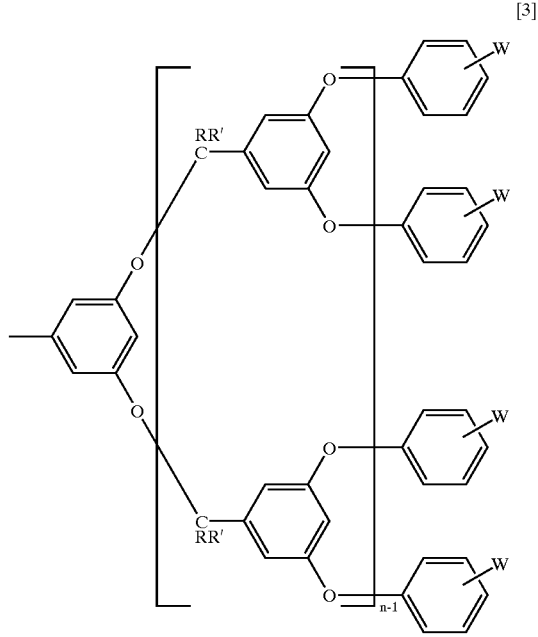

[3]

wherein R and R' each represent a hydrogen atom or a hydrocarbon group and maybe identical or different, W represents an anionic group when the charge c is negative (−), or W represents a cationic group when the charge c is positive (+), each W may be bound by a spacer molecule chain, and n represents an integer).

Further, the present invention provides, secondly, the above polymeric micellar structure, wherein the anionic group is an acid anionic group, thirdly, the above polymeric micellar structure, wherein the cationic group is represented by the following formula:

$N^+(CR^1R^2R^3)_3$ ($R^1$, $R^2$ and $R^3$, which may be identical or different, each represent a hydrocarbon group), fourthly, the above polymeric micellar structure wherein the spacer molecule chain is represented by the following formula;

$C(Z)Z'R^4(CR^5R^6)_n$ (Z and Z' may be identical or different and each represent at least one atom of O, S and N, $R^4$ represents a hydrocarbon group when Z' is an N atom, $R^5$ and $R^6$ may be the same or different and represent a hydrogen atom or a hydrocarbon group, and m represents 0 or an integer of 1 or more), and fifthly, the above polymeric micellar structure wherein n is an integer of 25 or less.

Furthermore, the present invention sixthly provides the above polymeric micellar structure, which is an electrostatically bonded polymeric micelle of an ionic porphyrin dendrimer and a water-soluble polyaminoacid-type polymer, seventhly, the above polymeric micellar structure wherein the water-soluble polyaminoacid-type polymer is a block copolymer of a poly alkylene glycol and a polyaminoacid, eighthly, more specifically, the polymeric micellar structure, which is an electrostatically bonded polymeric micelle of an anionic porphyrin dendrimer and a water-soluble polyethylene glycol-poly-L-lysine block polymer ([PEG-PLL(12-31)]), and ninthly, the polymeric micellar structure, which is an electrostatically bonded polymeric micelle of a cationic porphyrin dendrimer and a polyethylene glycol-poly-L-aspartic acid block polymer ([PEG-P(Asp) (12-28)]).

Moreover, the present invention tenthly provides an agent for photodynamic treatment, comprising, as an active ingredient, any one of the above polymeric micellar structure or a substance containing the same.

BEST MODE FOR CARRYING OUT THE INVENTION

Figure 1:
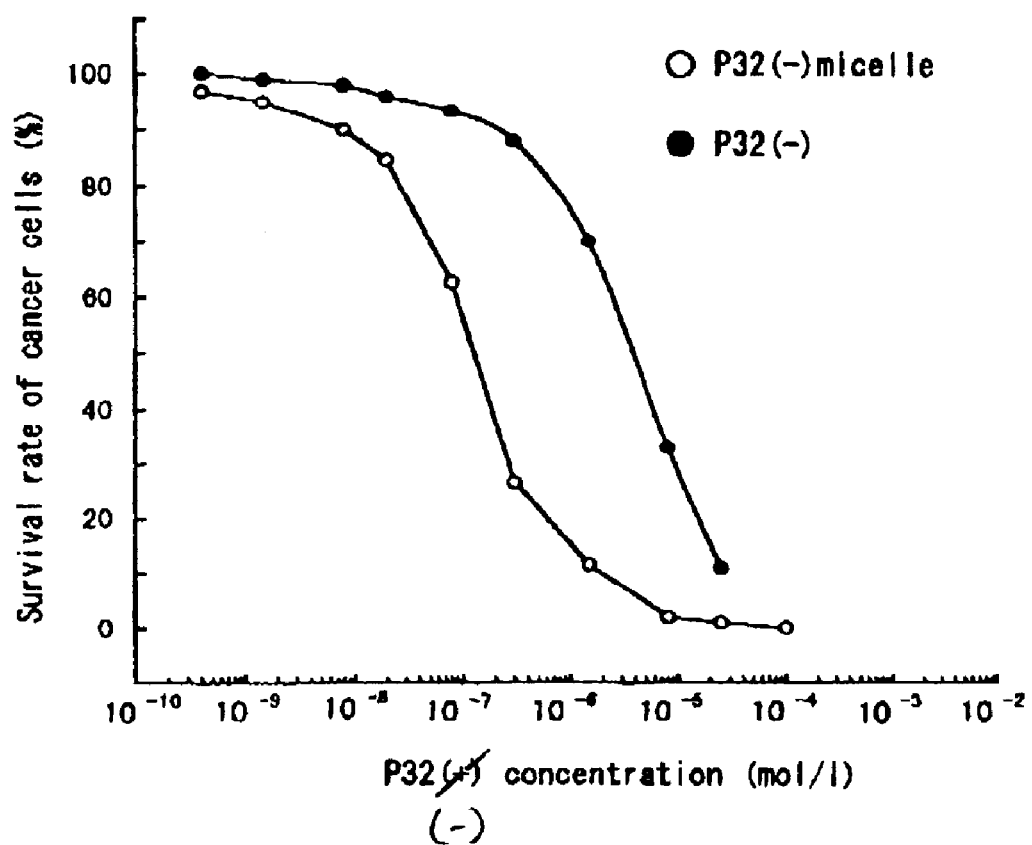
FIG. 1 is a graph showing the survival rate of cancer cells under irradiation, when an electrostatically bonded polymeric micelle and an anionic porphyrin dendrimer were respectively added, in the Example of the present invention.

The polymeric micellar structure of the present application comprises the ionic porphyrin dendrimer represented by the above-described general formula [1], but the central metal M in the metal porphyrin dendrimer represented by the general formula [2] may be any atom. Since the excitation state and the oxidation mode of oxygen varies depending on the type of central atom, various metals such as Zn, Mg, Fe, Cu, Co, Ni and Mn are applicable. A metal capable of forming singlet oxygen while forming a stable porphyrin compound in vivo is preferable, and Zn, which shows high energy at photoexcitation and is advantageous in the formation of singlet oxygen, is especially favorable.

Further, the porphyrin compound of the present invention may be one that is excitable with light of any wavelength, such as ultraviolet, visible, infrared or the like; a compound that is photoreactive in the wavelength region of ultraviolet or visible light is preferable, since their light sources are less costly and easy to handle.

At least one of $R_1$, $R_2$, $R_3$ and $R_4$ in general formula [2] is an aryl ether dendro-subunit represented by general formula [3]. In this aryl ether dendro-subunit, when the foregoing R and R' are both hydrocarbon groups, they are preferably alkyl groups. Further, they are appropriately alkyl groups having 25 or less carbon atoms. In addition, when the foregoing W is an anionic group, an appropriate example would be an acid anionic group, specific examples of which are $CO^{2-}$, $PO_4^{2-}$, $MPO_4^-$, $SO_4^{2-}$, $HSO_4^-$, $SO_3^-$ and the like. When W is a cationic group, it may be an amino group, an ammonium group or the like; for example, when it is a group represented by $N^+(CR^1R^2R^3)_3$ as mentioned above, $R_1$, $R^2$ and $R^3$ are each alkyl groups; more specific examples would be those having 25 or less carbon atoms, and further, those having 10 or less carbon atoms.

Whether W is an anionic group or a cationic group, it may be bound to the benzene ring through a spacer molecule chain. An example of such spacer molecule chain may be one represented by $C(Z)Z'R^4(CR^5R^6)_n$ as described above, and when $R^4$, $R^5$ and $R^6$ are each hydrocarbon groups, the numbers of carbon atom are preferably 25 or less, more preferably, 10 or less. Examples of the spacer molecule chain represented by this general formula include —CO—O—$(CR^5R^6)_n$—, —CO—$NR^4$—$(CR^5R^6)_n$— and the like. It is appropriate that m is 0 or an integer of 1 to 25.

For example, in the foregoing aryl ether dendro-subunit, the coefficient n in the general formula [3] is not particularly limited. However, when it is too large, its synthesis becomes difficult due to steric hindrance, and therefore, an integer of 25 or less is generally preferable.

The polymeric micellar structure comprising the ionic porphyrin dendrimer of the present invention may be an electrostatically bonded polymeric micelle of such dendrimers and a water-soluble ionic polymer.

In the present invention, more specifically, as such polymeric micellar structure, a micellar structure of the above ionic porphyrin dendrimer and a water-soluble polyaminoacid-type polymer containing its counter ion is mentioned. Examples thereof include a micellar structure of an anionic porphyrin dendrimer and a water-soluble polyethylene glycol-polylysine block polymer, a micellar structure of a cationic porphyrin dendrimer and a water-soluble polyethylene glycol-polyaspartic acid block polymer, and the like.

The polymeric micellar structure for photodynamic treatment of the present invention comprises the porphyrin dendrimer in its center, and forms a micelle with various drug delivery systems such as liposomes and various polymers, thereby increasing its affinity to the target site such as cancers and tumors and allowing the ionic porphyrin compounds for photodynamic treatment to be used more easily as anticancer agents.

Here, the compound that is electrostatically bonded may be any compound as long as it is capable of ionically bonding to the groups on the periphery of the porphyrin dendrimer to form stable micelles, and does not inhibit the photoreaction of the porphyrin dendrimer (i.e. it shows no absorption at the wavelength region of irradiation), and further, does not exhibit toxicity in vivo. For example, when the charge on the periphery of the porphyrin dendrimer is negative (−), as stated earlier, the polymeric micellar structure for photodynamic treatment of the present invention is preferably composed of the anionic porphyrin dendrimer and a water-soluble polyethylene glycol-poly-L-lysine block polymer ([PEG-PLL(12-31)]). Further, when the charge on the periphery of the porphyrin dendrimer is positive (+), as stated earlier, the polymeric micellar structure for photodynamic treatment of the present invention is preferably composed of the cationic porphyrin dendrimer and polyethylene glycol-poly-L-aspartic acid block polymer ([PEG-P(Asp)(12-28)]).

The ionic porphyrin dendrimer contained in the polymeric micellar structure for photodynamic treatment of the present invention may be synthesized by any known method, such as the divergent method (D. A. Tomalia, et. al., *Polymer J.*, 17, 117 (1985)), wherein the dendrimer is formed from the center toward its outer layer, and the convergent method (C. Hawker et. al., *J. Chem. Soc. Chem. Commun.*, 1990, 1010 (1990)), wherein the dendrimer is formed from the outside toward its center. The divergent method, which enables the dendrimer to grow by repeating a reaction, is preferable.

Specifically, in the ionic porphyrin dendrimer of the present invention, the dendrimer moiety may be obtained by repeating the procedure of reacting benzyl bromide containing an ionic group with the dendrimer, 3,5-dihydroxybenzyl alcohol, then brominating the —OH group in benzyl alcohol and reacting this group with 3,5-dihydroxybenzyl alcohol. Reaction of this dendrimer moiety with the porphyrin derivative, and insertion of a metal, gives the desired ionic porphyrin dendrimer Moreover, in the polymeric micellar structure of the present invention, the polymeric electrolyte compound that is bonded with the porphyrin dendrimer to form a micellar structure is not limited to the foregoing compounds. Polymers made to express anionic, amphoteric, or cationic properties by adjusting the pH of polyamino acids such as polyaspartic acid, polyglutamic acid, polylysine, polyarginine, polyhistidine and the like, anionic polymers such as polymalic acid, polyacrylic acid, polymethacrylic acid and polyallyl sulfonate as in polystyrene sulfonate, polyvinyl sulfate and the like, and cationic polymers such as polyethyleneimine, polyvinylamine, polyallylamine, polyvinylimidazole and the like are listed as examples. Further, block copolymers of these ionic polymers and nonionic water-soluble polymers may also be used effectively. These ionic block copolymers are excellent in biocompatibility, and are especially preferable as the polymeric electrolyte.

The present invention is further illustrated in more detail by referring to the following Examples. It should be needless to say that the invention is not limited to the following Examples and various details and embodiments are possible.

EXAMPLES

Reference Example

Synthesis of Porphyrin Dendrimers

A dendron monomer was prepared according to chemical formula [4a], and a dendron was formed according to [4b]. The resulting dendron and a porphyrin derivative were reacted in he presence of $K_2CO_3$, and the resulting porphyrin dendrimer was reacted with $Zn(OAc)_2$ to insert Zn to the porphyrin center (chemical formula [5]). Then, the end-groups of the anionic dendron were converted to $COO^-$ under a KOH aqueous solution to obtain the anionic porphyrin dendrimer ([32(−) (L3)$_4$PZn]).

Further, the anionic porphyrin dendrimer was reacted with $(CH_3)_2NCH_2CH_2NH_2$ and $CH_3I$, consecutively, and followed by ion exchange, to obtain the cationic porphyrin dendrimer ([32(+)(L3)$_4$PZn]) containing $CONH(CH_2)N_2(CH_3)_2$ at its end.

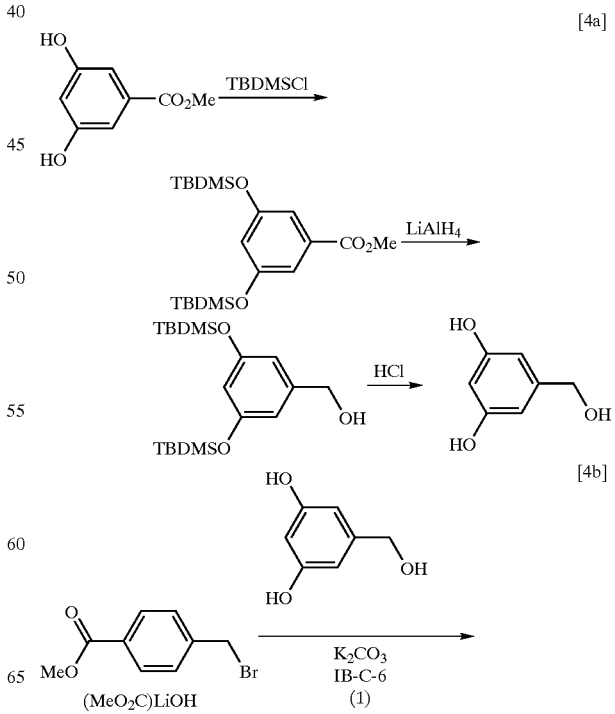

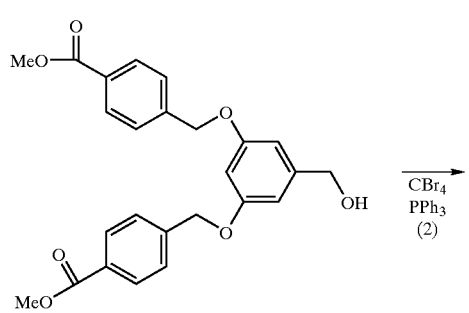

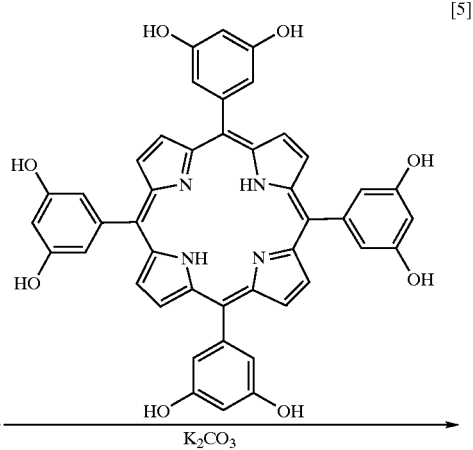

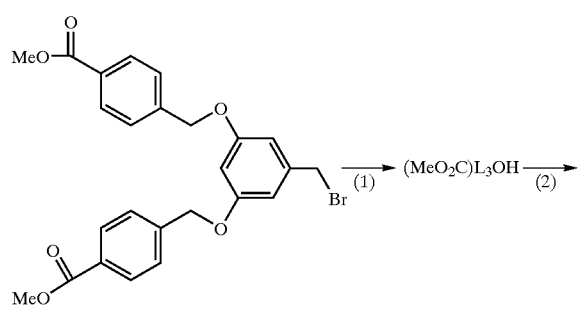

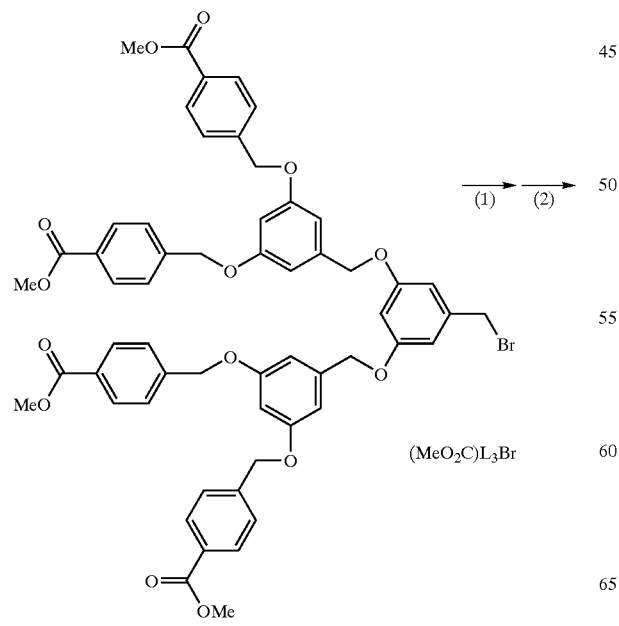

Example 1

Preparation of Electrostatically Bonded Polymeric Micelles of Anionic Porphyrin Dendrimer [32(−)(L3)$_4$PZn] and Water-soluble Polyethylene Glycol-poly-L-lysine Block Polymer [PEG-PLL(12-31)]

[PEG-PLL(12-31)] (composed of a PEG block with a molecular weight of 12000 g/mol and a polylysine block of 31 lysine units) was dissolved in NaH$_3$PO$_3$ to a concentration of 10 mM.

A porphyrin dendrimer expressed by the general formulas [1], [2] and [3], wherein M represents a metal zinc (Zn) atom, R and R' represent hydrogen atoms, W represents an anionic group (X*CO$_2^−$) and n represents 3, which may also be represented by the following formula

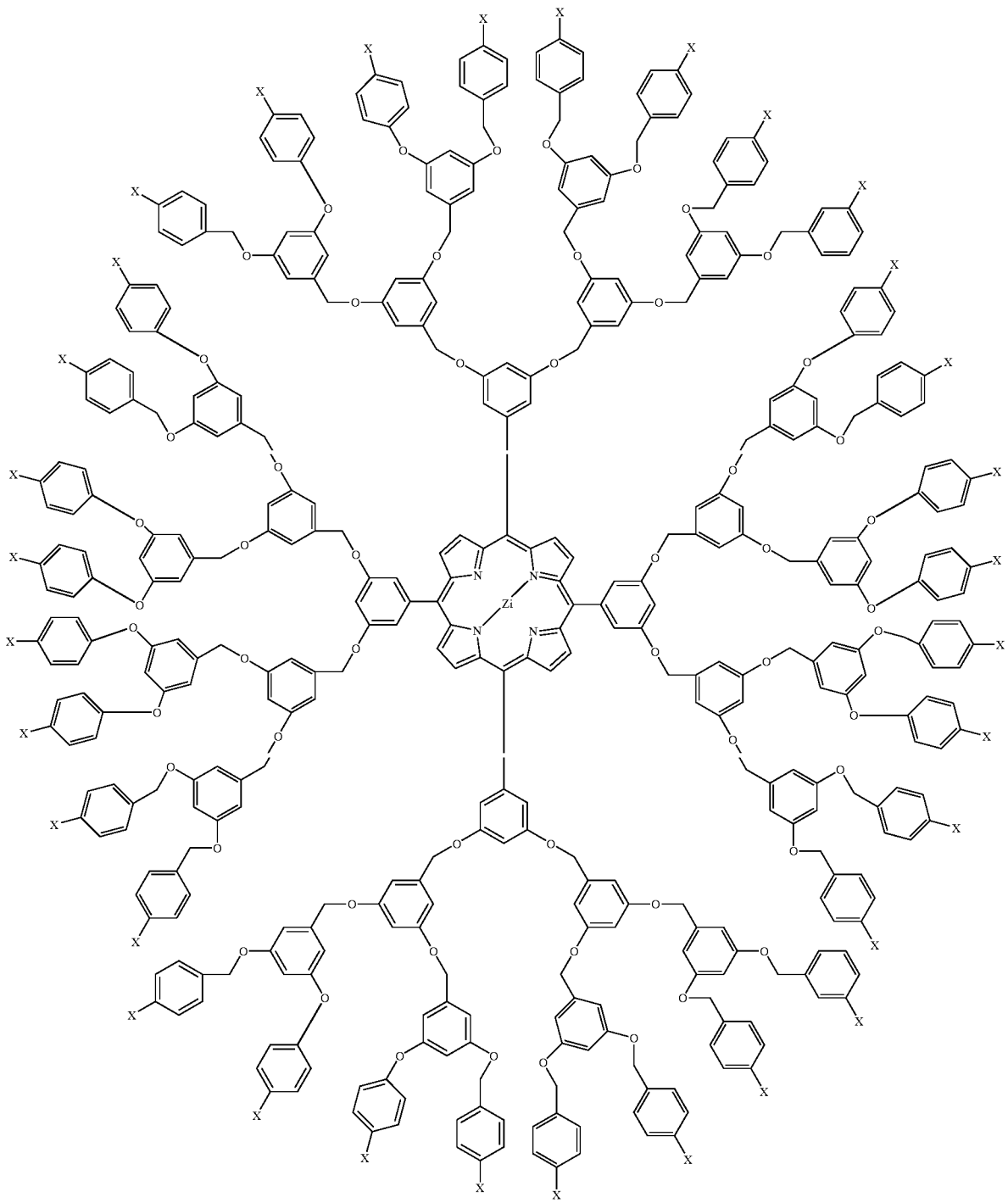

and also by the formula [32(−)(L3)$_4$PZn], was dissolved in NaH$_3$PO$_4$ to a concentration of 10 mM, followed by the addition of NaOH(160 μl, 0.1 N), which was dissolved completely.

The resulting solution was clear and retained its stability even after a few days. The pH was 7.29, and [32(−)(L3)$_4$PZn] by itself was insoluble at this pH region. This result indicated that in the clear solution, a polymeric micellar structure was formed by the electrostatic interaction between [32(−)(L3)$_4$PZn] and [PEG-PLL(12-31)], and its diameter was determined to be 120 nm through dynamic light scattering measurement.

Further, a test solution was prepared by adding 50 μl of solvent and 50 μl of lung cancer cells (Lewis Lung Carcinoma, 50000 cells/ml) to a phosphate buffer solution (PBS) of the electrostatically bonded polymeric micelle of [32(−)(L3)$_4$PZn] and [PEG-PLL(12-31)]. This solution was irradiated with light at a wavelength of 380 to 700 nm for 10 minutes, and incubated at 37° C. for 48 hours, after which the survival rate of the lung cancer cells were measured by the MTT assay tent method (Mitochondrion Respiration Test).

Comparative Example 1

As in Example 1, a test solution containing the anionic porphyrin dendrimer [32(−)(L3)$_4$PZn] instead of the electrostatically bonded polymeric micelle was prepared, and subjected to cell activity test.

The results of the cell activity tests in Example 1 and comparative Example 1 are shown in FIG. 1.

The amount of drug at which the survival rate of the added cancer cells reach 50% (Effective Dose: $ED_{50}$) after 48 hours of incubation was $2\times10^{-7}$ for the polymeric micellar structure of the present invention (Example 1). It was further confirmed that the destruction effect by light irradiation of the porphyrin dendrimer forming a micelle was much greater than that of the porphyrin dendrimer that does not form a polymeric micelle structure.

Example 2

Preparation of Electrostatically Bonded Polymeric Micelles of Cationic Porphyrin Dendrimer [32(+)(L3)$_4$PZn] and Polyethylene Glycol-poly-L-aspartic Acid Block Polymer [PE(-P(Asp)(12-28)]

[PEG-P(Asp)(12-28)] (composed of a block with a molecular weight of 1200 g/mol and a polyaspartic acid block of 28aspartic acid units) was used instead of [PEG-PLL(12-31)] in Example 1, and instead of [32(−)(L3)$_4$PZn], a porphyrin dendrimer wherein W represents a cation (Y=$N^+(CH_3)_3$) bonded through a spacer molecule chain —CO—$(CH_2)_2$— and n represents 3,and is expressed by the following formula

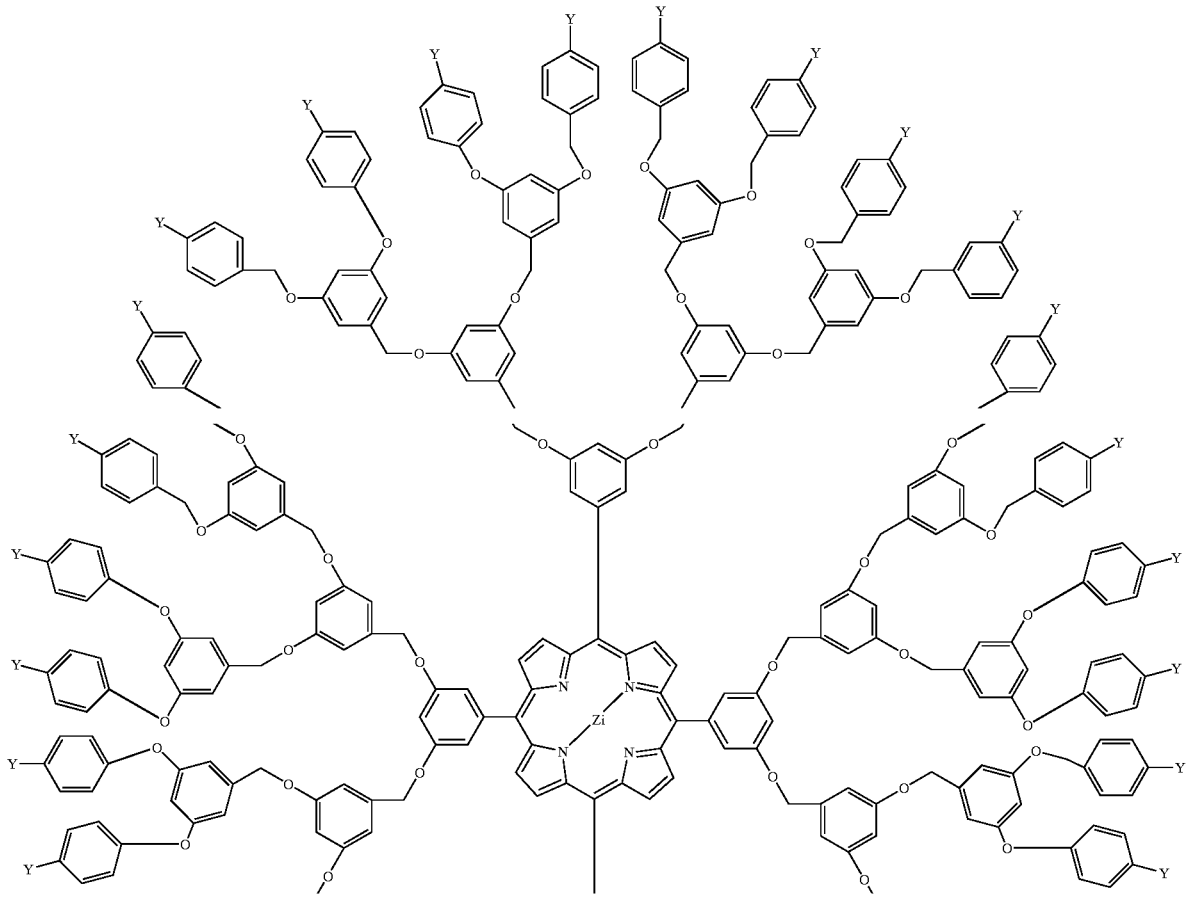

-continued

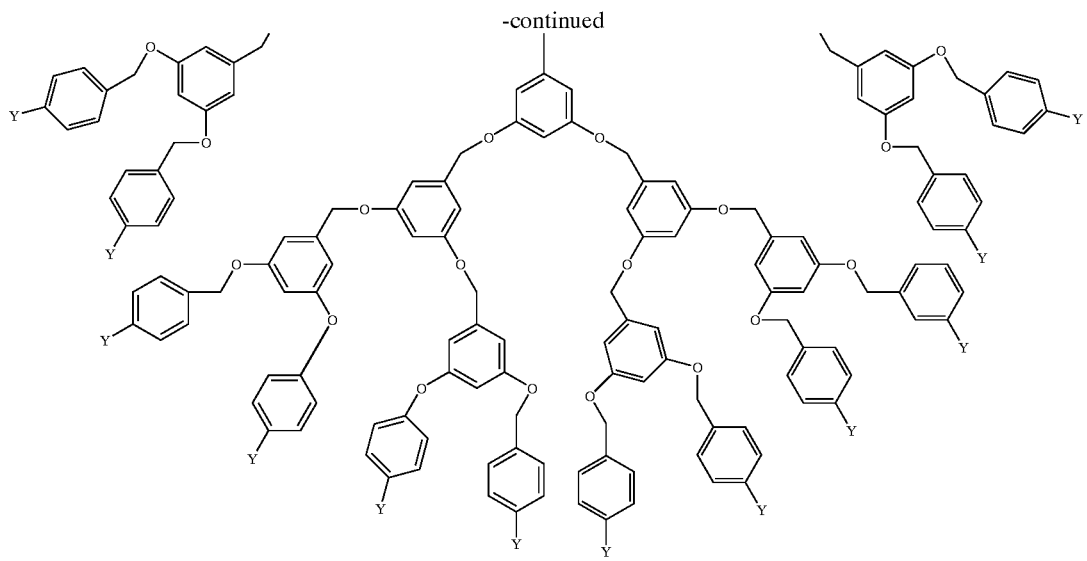

or by the formula [32(+)(L3)₄PZn], was used, which were then mixed under the above-described conditions.

The resulting solution was clear and retained its stability even after a few days. The pH was 6.3. Further, in the clear solution, an electrostatically bonded complex micelle of [32(+)(L3)₄PZn] and [PEG-P(Asp)(12-28)] was formed, the diameter of which was determined as 116.5 nm by dynamic light scattering measurement.

Further, a test solution was prepared by adding 50 μl of solvent and 50 μl of lung cancer cells (Lewis Lung Carcinoma, 50000 cells/ml) to a phosphate buffer solution (PBS) of the electrostatically bonded complex micelle of [32(+)(L3)₄PZn] and [PEG-P(Asp)(12-28)]. This solution was irradiated with light at a wavelength of 380 to 700 nm for 10 minutes, and incubated at 37° C. for 48 hours, after which the survival rate of the lung cancer cells were measured by the MTT assay test method (Mitochondrion Respiration Test).

Comparative Examples 2 and 3

The same test was also performed for the micelle test solutions without conducting the 10 minutes light irradiation (Comparative Example 2). Also, in the manner described in Example 2, a test solution containing the cationic porphyrin dendrimer [32(+)(L3)₄PZn] instead of the electrostatically bonded polymeric micelle was prepared, and subjected to cell activity test (Comparative Example 3).

Figure 2:
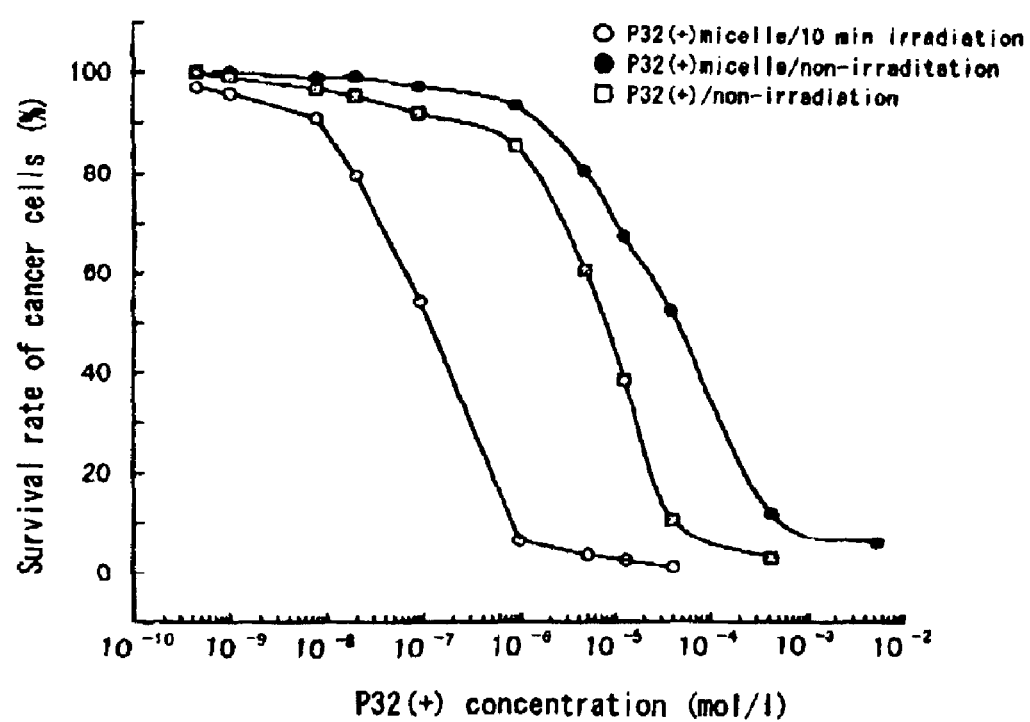
FIG. 2 is a graph showing the survival rate of cancer cells under irradiation and non-irradiation, when an electrostatically bonded polymeric micelle was added, and under non-irradiation when a cationic porphyrin dendrimer was added, in the Example of the present invention.

The results of the cell activity test in Example 2 and Comparative Examples 2 and 3 are shown in FIG. 2.

After 48 hours of the incubation, the $ED_{50}$ was $1.9 \times 10^{-7}$ for the electrostatically bonded polymeric micellar structure of [32(+)(L3)₄PZn] and [PEG-P(Asp)(12-28)] (Example 2). It was then confirmed that the carcinoma destruction effect increased greatly by the irradiation of the porphyrin dendrimer, as compared to the non-irradiated micelle (Comparative Example 2). Moreover, by comparing it with that for the solution containing [32(+)(L3) ₄PZn] alone (Comparative Example 3), it was confirmed that its safety as a compound for photodynamic treatment, when not irradiated, increased greatly by the formation of the polymeric micellar structure.

INDUSTRIAL APPLICABILITY

As has been described in detail, the present invention provides a polymeric micellar structure for photodynamic treatment, which contains a porphyrin compound for photodynamic treatment that is capable of selectively destroying target cells such as cancer cells, can efficiently deliver the same to the target cells, is easy to use as a drug and is stable in water.

What is claimed is:

1. A polymeric micellar structure comprising an ionic porphydrin dendrimer represented by general formula [1]

$$q(c)PM \qquad [1]$$

(wherein q represents the number of charged atoms on the periphery of the dendrimer, c represents a negative (−) or positive (+) charge; and PM is represented by the following general formula [2];

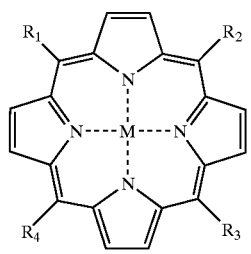

[2]

wherein M represents two hydrogen atoms or a metal atom; and $R_1$, $R_2$, $R_3$ and $R_4$ represent a hydrogen atom or aryl ether dendro-subunits that may be identical or different, at least one of $R_1$, $R_2$, $R_3$ and $R_4$ is an aryl ether dendrosubunit, which is represented by the following general formula [3];

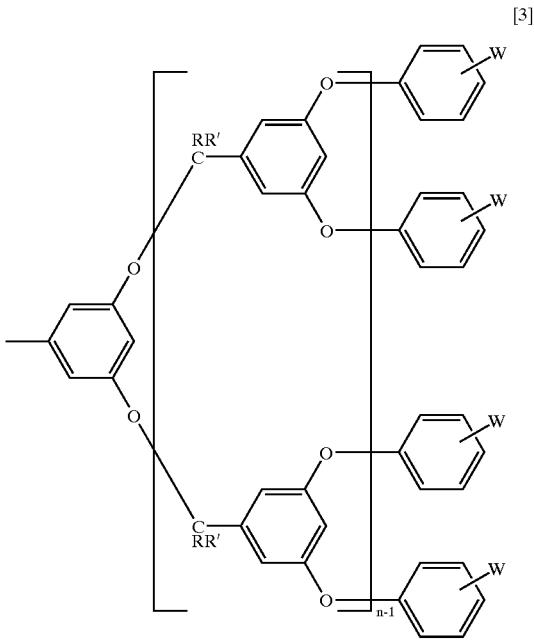

wherein R and R' each represent a hydrogen atom or a hydrocarbon group and may be identical or different, W represents an anionic group when the charge c is negative (−), or W represents a cationic group when the charge c is positive (−), each W may be bound by a spacer molecule chain, and n represents an integer) and a water-soluble polyaminoacid-type polymer.

2. The polymeric micellar structure of claim 1, wherein the anionic group is an acid anionic group.

3. The polymeric micellar structure of claim 1, wherein the cationic group is represented by the following formula;

$$N^+(CR^1R^2R^3)_3$$

($R^1$, $R^2$ and $R^3$, which may be identical or different, each represent a hydrocarbon group).

4. The polymeric micellar structure of claim 1, wherein the spacer molecule chain is represented by the following formula;

$$C(Z)Z'R^4(CR^5R^6)_m$$

(Z and Z' may be identical or different and each represent at least one atom of O, S and N, $R^4$ represents a hydrocarbon group when Z' is an N atom, $R^5$ and $R^6$ may be the same or different and represent a hydrogen atom or a hydrocarbon group, and m represents 0 or an integer of 1 or more.

5. The polymeric micellar structure of claim 1, wherein n is an integer of 25 or less.

6. The polymeric micellar structure of claim 2, wherein n is an integer of 25 or less.

7. The polymeric micellar structure of claim 3, wherein n is an integer of 25 or less.

8. The polymeric micellar structure of claim 4, wherein n is an integer of 25 or less.

9. The polymeric micellar structure of claim 1, wherein the water-soluble polyaminoacid-type polymer is a block copolymer of a polyalkylene glycol and a polyaminoacid.

10. The polymeric micellar structure of claim 9, wherein the block copolymer of polyalkylene glycol and polyaminoacid is water-soluble polyethylene glycol-poly-L-lysine block polymer ([PEG-PLL(12-31)]).

11. The polymeric micellar structure of claim 9, wherein the block copolymer of polyalkylene glycol and polyaminoacid is polyethylene glycol-poly-L-aspartic acid block polymer ([PEG-P(Asp)(12-28)]).

12. An agent for photodynamic treatment comprising, as an active ingredient, the polymeric micellar structure of claim 1, for a substance containing the same.

* * * * *